United States Patent [19]

Becker

[11] 4,231,368
[45] Nov. 4, 1980

[54] DEVICE FOR INTRAMUSCULAR INJECTIONS, ESPECIALLY OF INSULIN

[76] Inventor: Michael Becker, Brucknerstrasse 6, 5020 Frechen-Grefrath, Fed. Rep. of Germany

[21] Appl. No.: 22,374

[22] Filed: Mar. 20, 1979

[30] Foreign Application Priority Data

Mar. 23, 1978 [DE] Fed. Rep. of Germany ....... 2812729

[51] Int. Cl.³ .............................................. A61M 5/00
[52] U.S. Cl. ................................. 128/218 A; 128/236
[58] Field of Search ................... 128/236, 234, 218 A, 128/218 F, 215, 224

[56] References Cited

U.S. PATENT DOCUMENTS 4,067,334   1/1978   Haller .............................. 128/218 A

FOREIGN PATENT DOCUMENTS 621145   4/1933   Fed. Rep. of Germany ........... 128/236
819629  10/1937   France ..................................... 128/236
86184    7/1955   Norway ................................. 128/218 F
143084   5/1920   United Kingdom ................. 128/218 F
256011   8/1926   United Kingdom ..................... 128/236

*Primary Examiner*—John D. Yasko
*Attorney, Agent, or Firm*—Frishauf, Holtz Goodman & Woodward

[57] ABSTRACT

A pistol-like casing provides for mounting a tubular holder containing a syringe in the gun barrel portion of the casing so it may be cocked in the withdrawn position against the force of a spring and released by movement of an arresting pawl. Pulling back a trigger advances a push rod that first trips the pawl, then brings force to bear against the piston rod of the syringe. After the needle is driven into the skin by the release of the pawl and the actuating mechanism has been brought to bear against the syringe piston-rod, the injection of the syringe contents can proceed under control of hand feel without any necessity of changing or shifting the hand grip, by simply continuing to pull the trigger back.

5 Claims, 8 Drawing Figures

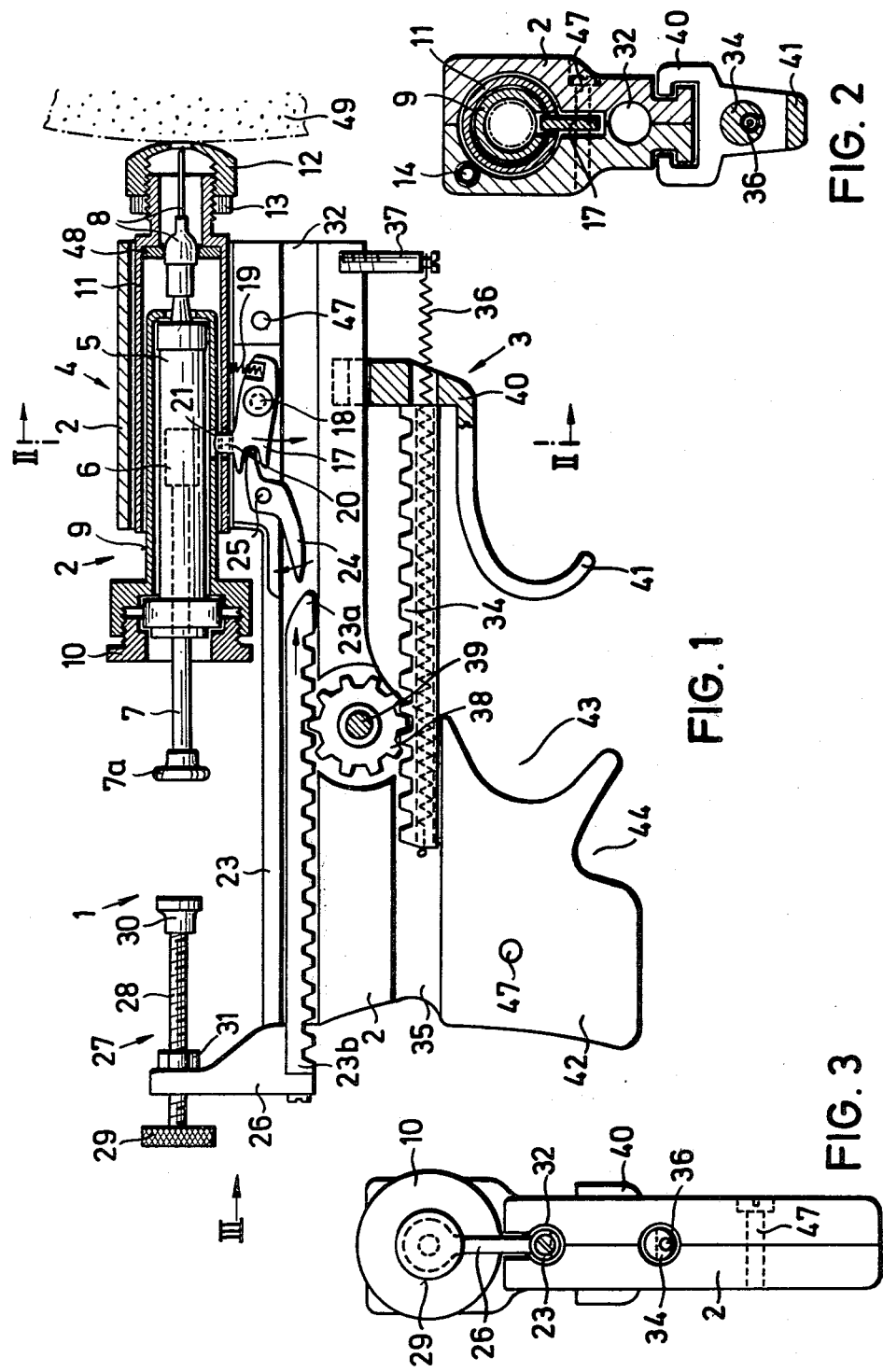

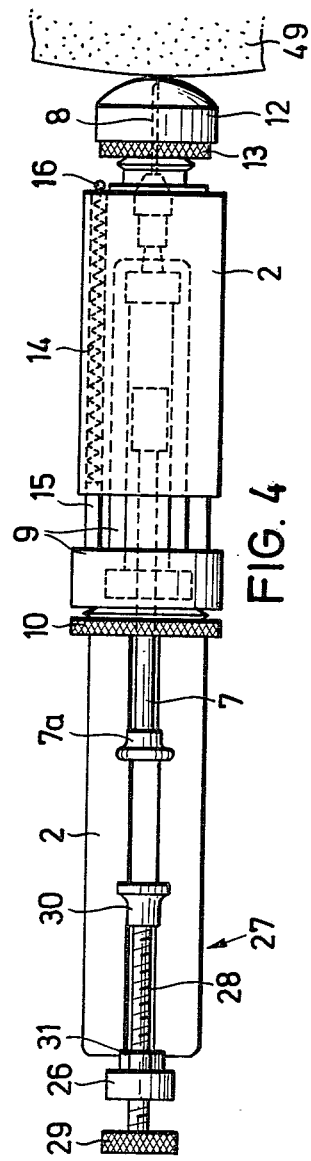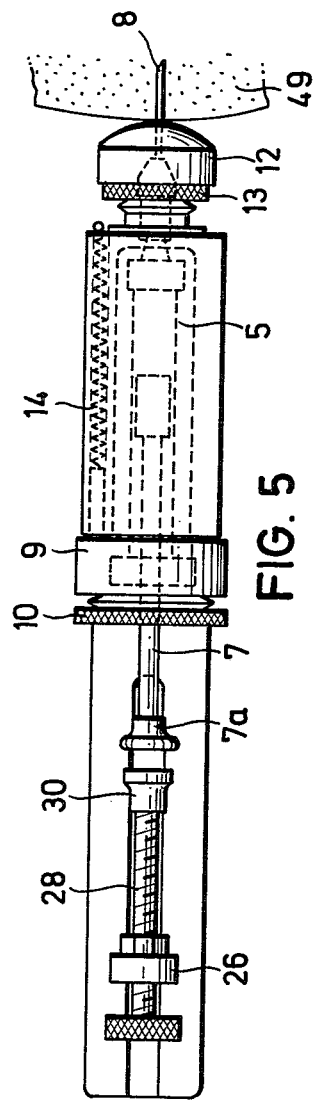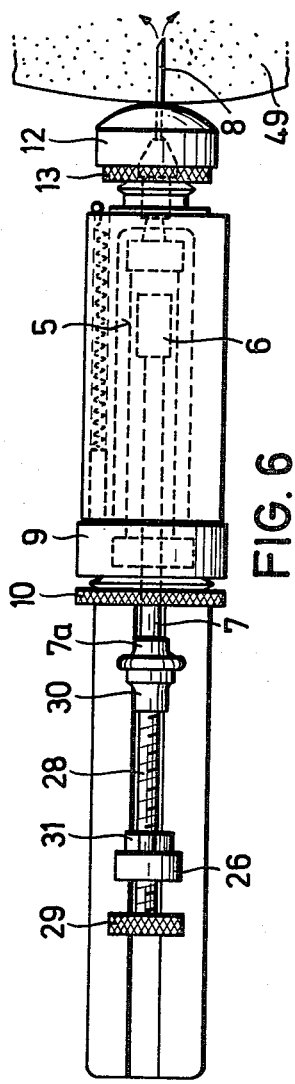

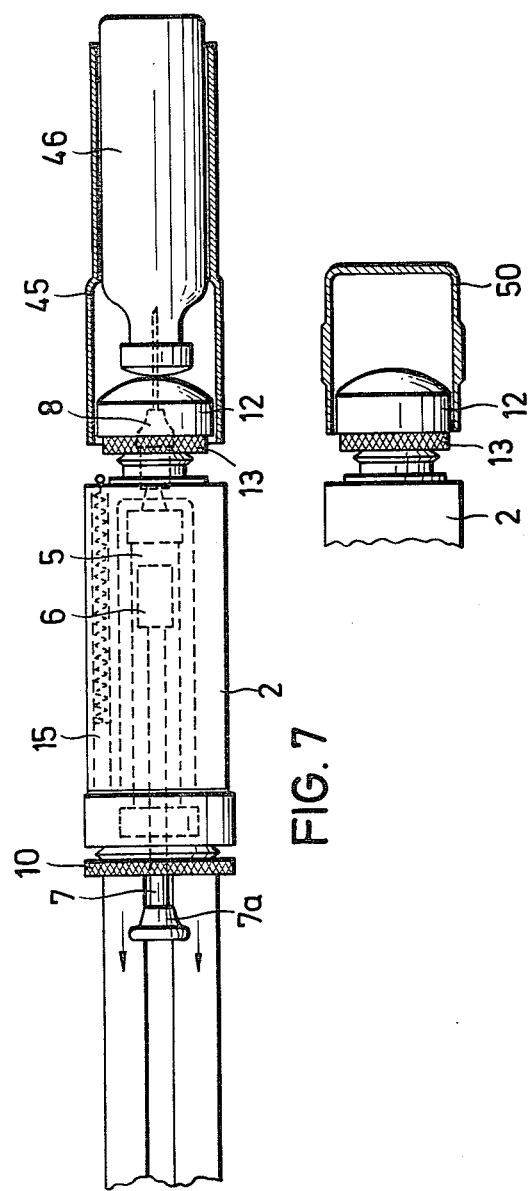

DEVICE FOR INTRAMUSCULAR INJECTIONS, ESPECIALLY OF INSULIN

This invention concerns an intramuscular injection device capable of fulfilling the many requirements for all circumstances in which insulin injections are made and, particularly, a device utilizing a readily insertable and removable syringe and providing an actuating mechanism both for quick insertion of the needle of the syringe and, thereafter, driving forward the piston rod of the syringe piston.

The injection devices are known for mounting and actuating a syringe in which a cylindrical holder is provided for containing the syringe. In these devices, the holder is positioned in the device under spring pressure or tension and cocked in the withdrawn position of the needle by means of a pawl catch. The handling of an injection device thus cocked admits the possibility of releasing the catch lever by one finger of the same hand that holds the device while with another finger of the same hand, or a shift of the first finger to another place, the piston of the syringe can be pressed forward.

German published patent application DE-AS No. 15 66 606 describes an automatic injection device with a piston movable in the injection direction by means of a spring and a push-button fastened to the piston for pressing out the injection liquid. This device, however, is suitable only for use with ampoules; furthermore, the dispensing of the liquid is performed by means of a spring that is located in a cylinder filled with an auxiliary liquid of the kind conventional for hydraulic control. Regulation of the rate of dispensing is performed by throttling the hydraulic auxiliary liquid in a by-pass channel.

The German utility model, No. 76 38 511, shows a insulin injection device with a helical spring arranged to be tensioned before the injection with a catch-rod lockable against the spring pressure. The spring is contained in a cylindrical spring housing, but is movable lengthwise therein. Such an injection device may in fact be used with one hand, but both the driving of the needle into the body and the injection of the medicament contained in the injector are performed automatically in a single course of movement. With such an automatic device, the dispensing of the medicament cannot be interrupted by hand.

It is an object of the present invention to provide a intramuscular injection device, suitable particularly for the injection of insulin, with a syringe capable of operation with only one hand and with which, after a rapid puncture movement inserting the needle, the dispensing of the medicament may be performed quickly or slowly, at will, even with interposition of pauses.

SUMMARY OF THE INVENTION

Briefly, an injection device, of the kind in which a cylindrical holder contains a syringe and is subjected to the force of a spring and maintainable in the withdrawn position by means of a catch-pawl, is further developed by the present invention by providing a hand actuation mechanism for bringing force to bear first on the catch-pawl and then on the piston-rod of the syringe, the mechanism being contained in a casing providing a gun-barrel guidway for the syringe holder and a convenient gripfor holding the device by the same hand that operates the mechanism. Furthermore, the mechanism is such that a single continuous movement applied by one and the same finger will operate both the release of the catch-pawl and the dispensing of the medicament.

By such constitution of the injection device, single-handed manipulation of the device is made possible together with a combination of advantages is particularly important for the injection of insulin. With one and the same actuating mechanism it is possible, with the same finger, both to release a rapid puncture movement of the injection needle and then to carry out at will the displacement of the piston of the syringe for driving the medicament into the muscle, so that a shifting or repositioning of the hand or of the operating finger is not necessary. The injection operation may be carried out entirely by feel, which is particularly important for diabetics, because insulin must be injected slowly.

The injection device is handy to me and the injection may be performed in a simple and safe manner, even in locations of the human body that are difficult of access.

According to further features of the invention, for combining a rapid puncture movement for the injection needle and a slow pressing forward of the medicament out of the syringe, a push-rod displaceable lengthwise is provided in the casing of the apparatus in such a way that the forward end of the push-rod may be brought to bear on the catch-pawl while its rear extremity is equipped for engaging the piston-rod of the syringe. The push-rod may be connected to an actuating the rod system displaceable relative to the casing. This is advantageously constituted by providing both the push-rod and also an actuating rod in the form of rack (toothed) rods and interposing a gear wheel between them for mechanical force transfer, while one of the rack rods is subjected to the force of spring. In this manner very good feel of the injection process is obtained in actuation of the device, because hand pressure is directly transferred to the piston of the injection syringe through the toothed rods. Instead of the single gear, it is also possible to provide more gears for gearing up or down the movement of the push rod relative to the actuating rod.

The rack rods are conveniently arranged facing each other, oriented lengthwise of the device, and one above and the other below the interposed gear. A particular feature of this arrangement is that the lower rack rod may be guided by a slider, movable lengthwise with respect to the casing and, preferably, constituted as a trigger member, while the casing has a pistol-like grip portion. By such combination of features of the casing and the actuating mechanism, it is possible to hold the injection device in hand before operation easily and without concern and, also, to perform both the "shot" insertion of the needle and the injection of the medicament with one finger without changing the hand grip. The injection needle is caused to puncture the skin by means of the same trigger by which a further pull movement produces injection of the medicament, easily performed according to any prescribed medical directions and fully under control in response to hand feel.

The push-rod or upper rack rod is advantageously furnished with a heel or a bracket equipped with an adjusting device in the form of a threaded spindle with a tip for engaging the syringe, so that the amount of movement of the trigger between the pawl release and the beginning of the injection of the medicament can be selected with reference to the initial position of the piston rod of the syringe.

The tubular holder for the syringe is preferably arranged to slide within an intermediate cylindrical shell having a cap portion serving as the tip shield of the device. This shell fits into a cavity in the casing resembling a piston barrel, while the syringe holder is directly connected with the casing by a tension spring that pulls it forward. The cap portion of the shell serves to protect the projecting needle of the syringe and, at the same time, to allow an additional tubular piece to be mounted in front of the cap, in order to support a supply container, from which the syringe may be filled with medicament. Such an additional accessory shell, or container, makes it easy to use the syringe suction for filling.

The invention is further described, by way of illustrative example, with reference to the annexed drawings in which:

FIG. 1 is a side elevation diagrammatically showing an illustrative example of an injection device according to the invention;

FIG. 2 is a cross-section of the device of FIG. 1, on the line II—II of FIG. 1;

FIG. 3 is an end view of the device in FIG. 1, in the direction indicated at III in FIG. 1;

FIGS. 4, 5 and 6 are top views of the device of FIG. 1 diagrammatically showing different stages of actuation of the device; and FIGS. 7 and 8 are top views of the front end of the device of FIG. 1 showing, in section, push-on mountings for a filling container (FIG. 7) and for a dust cap (FIG. 8).

As shown particularly in FIGS. 1, 2 and 3, the intramuscular injection device of the present invention has a casing 2 within which are combined apparatus for quick puncturing insertion of the injection needle and, also, a hand-operable mechanism 3 for controlling the injection of medicament. The syringe 4, which is composed of a syringe container 5, a piston 6, a piston-rod 7 equipped with a knob 7a, and an injection needle 8, is mounted in a cylindrical holder 9, and can be clamped fast therein by which of a threaded bushing 10. The holder 9 is the movable member of a barrel mount which includes a shell 11 in which the holder 9 is axially movable. The shell 11 has a threaded cap 12 at its forward end which projects out of the casing 2 and a clamping nut 3 which serves to fix the cap 12 in place. The cap 12 serves to protect the injection needle 8. The shell 11 fits in the cylindrical barrel cavity provided in the front upper part of the casing 2. It is a guide guide for the movement of the holder 9 and of the needle 8 projecting therefrom, but it is evident that the holder 9 could also be arranged to be guided directly by the casing 2, which could similarly carry a bushing for guiding the needle 8 and mounting the threaded cap 12.

The spring 14 is mounted in a cylindrical bore in the casing 2 and is anchored, at one end, on the casing and, at the other end, to the pin 15 which is part of the rear flange of the cylindrical holder 9 (see FIGS. 4–6). At the same time the pin 15 serves to keep the holder 9 from rotating. The front anchor 16 of the spring is shown as a simple plug at the end of the bore in which the spring is housed.

A pawl catch 17, journaled at 18 in the casing, serves to secure the holder 9 in the withdrawn position of the syringe 4 contained therein. The pawl 17 is held in the positin shown by a spring 19. The pawl 17 has a cam 20 which penetrates into a slot 21 of the cylindrical holder 9, likewise passing through a slot in the shell 11.

A push-rod 23 is displaceably mounted in the casing 2. Its front end 23a indirectly engages the catch pawl 17 by means of an intermediate lever 24 that is pivoted at 25. The rear end 23b of the push-rod has a heel 26 equipped with an adjusting device 27, consisting of a threaded spindle 28, a knurled hand-knob 29 and a clamping nut 31. The front end of the spindle 28 carries a cap 30. Upon displacement of the push-rod 23, which is guided in a groove 32 in the casing, from its rest position, first the front end 23a bears indirectly on the catch-pawl to disengage it from the tubular holder 9, and then the rear end 23b and the bracket 26 bring the adjustable pusher 27 to bear on the knob 7a of the piston rod 7 of the syringe.

The manual actuation mechanism 3 advantageously make use of a rod linkage of the rack and gear type. The push-rod 23 accordingly provides one of two toothed rods, while the other toothed rod 34 is guided in the guideway 35 and is arranged to be held under the tension of the spring 36. The latter is anchored at one end by the pin 37 fixed in the casing 2, and at the other end at the rear extremity of the actuating rack rod 34. A small gear 38 mounted to a rotate on a bearing 39 in the casing 2 is located between the two rack rods 23 and 34. Instead of a single gear 38, a set of two or more gears for stepping up or down the actuation of movement can be used.

The rack rod 34 made fast to a slider 40 that is slidably mounted for motion lengthwise of the casing 2. The slider 40 is made in the form of a pull-trigger 41 and the casing 2 is provided with a pistol-like grip portion 42. The grip 42 is cut away at 43 so as to accept the trigger 41 in its fully drawn position, and there is another cut away 44 to make provision for the positioning of the middle finger of the hand of grasping the pistol grip 42.

As shown in FIG. 7, an auxiliary shell 45 can be pushed onto the cap 12 for the support of a supply container 46 in position for filling of the syringe. This arrangement assures the container 46 can be held in a position centered on the injection needle 8, so that the bending of the needle 8, upon withdrawing the medicament into the syringe 4, can be avoided. When the injection device is not in use, a dust cap 50 can be similarly pushed onto the cap 12 in order to protect the tip portion of the syringe from the introduction of dirt and other impurities.

The casing 2 is preferably composed of two parts that are held together by screws 47 as well as by the bearing pin 39.

OPERATION

To proceed with an injection, the filled syringe 4 is drawn back together with the container 9 in which it is held, until the cam 20 can fall into the slot 21 of the containing holder 9 while stretching the spring 14. Upon actuation of the trigger 41 (i.e., upon drawing back of the slider 40 together with the lower rack rod 34 by a pull applied by the index finger), the push rod 23 is driven forward across the gear 38 in the direction indicated by the arrow in FIG. 1. The front rod end 23 underrides and displaces the lever 24, by the pivoting movement of which, in the direction shown by another arrow, the cam 20 is pulled out of the slot 21 of the holder tube 9. The holder 9, with the syringe 4 that it contains, shoots forward under the effect of the spring 14 driving the injection needle 8 into the muscles 49 of the patient. Upon further pulling of the trigger 41 towards the position fitting in the cut-away 43 of the grip 42, the medicament contained in the syringe 4 is slowly injected with complete feel of the injection operation through the trigger 41, the injection beginning when the adjustable pusher 27 encounters the knob 7a of the piston-rod 7 of the syringe 4.

FIG. 4 shows the position of the parts of the device before the injection needle is driven into the body portion, whereas FIG. 5 illustrates a position in which, after the injection needle 8 is driven in, the suitably adjusted pusher 27 has closely approached the knob 7a of the syringe piston-rod 7. With further slow pulling back of the trigger 41, the pusher tip 30 encounters the knob 7a of the piston-rod 7 and presses forward the piston 6 within the syringe 4, as shown in FIG. 6.

The triggering of the needle puncture and the subsequent pressing in of the medicament out of the syringe 4 by means of the manual actuation mechanism 3 can be performed in a continuous pulling back of the trigger 41. According to the amount of medicament drawn up into the syringe 4, which is to say according to the position of the piston 6 and its piston rod 7, the pressing out of the medicament from the syringe 4 can proceed without further attention after the needle insertion step.

Upon the driving in of the needle 8, the tubular holder 9 and, with it, also the needle are damped just before the end of the insertion movement by a rubber bumper disk 48 located in the shell 11. The damping avoids any pyschologically disturbing shot noise and, likewise, any ultimate shaking off of the injection needle from its holding cone.

The insertion depth of the needle 8 can be set by the adjustability of the cap 12 and fixed with the clamping nut 13. At the same time, the injection needle is protected by the cap 12 which, as shown in FIGS. 7 and 8, also serves for the application of an auxiliary shell 45 for a renewed loading of the medicament into the syringe from the supply flask 46 held in the shell 45 and, of course, it is also possible to put a dust cap 50 onto the cap piece 12.

It is not necessary to fix the convenient intermediate shell 11 in the barrel of the casing 2, since in the withdrawn position it is held in position by the cam 21 of the pawl 17. By the time the pawl 17 is moved to release the catch cam 21, the cap 12 is already bearing upon the skin to be punctured. After the top of the holder 9 has moved to its forward position against the bumper washer 48, the tension of the spring 14 maintains that position and, at the same time, the rear flange of the holder 9 blocks away further movement of the holder 9 and the shell 11 together. As already mentioned, however, it is possible to provide a similar device in which the holder 9 moves in a bore directly provided by the casing 2.

The injection device described above can be used for any medicament which is to be injected by means of a syringe. With this injection device, it is possible to drive in the needle and to inject the serum or other medicament with one finger of the hand holding the device. Easy and convenient handling is provided for by the pistol-like shape of the device.

Injections may be performed with the device even at places on the human body which are difficult of access. Furthermore, the needle insertion depth can easily be set on the device and, in addition, it is possible with a single finger of the same hand to interrupt the injection at will or to carry it out to the end according to hand feel, which is important in the case of diabetics, especially for self-injection.

Particularly with use of the auxiliary shell for use in refilling the syringe, even a one-armed person can put the device to use, namely, by the following manipulations with one hand:

1. for sucking up the serum;
2. cocking the syringe; and
3. injecting.

The auxiliary shell further serves for storing the supply flask of serum and protects it against breakage, a feature which is important in connection with a carrying case or traveling. The injection device is so constituted that it may be taken along everywhere by the patient or by medical personnel in a small bag.

Although the invention has been described with particular reference to a single illustrative embodiment, it will be evident that modifications and variations are possible within the inventive concept. For example, the front end of the rod 23 could bear directly against a downward extension of the pawl 17 beyond its pivot if the barrel of the syringe and of the holder 9 were long enough to allow such a construction.

I claim:

1. A device for intramuscular injection capable of meeting the requirements of the administration of insulin, comprising a casing having a stationary grip member and, also, a guideway for displaceably mounting a syringe contained in a holder for a limited displacement in said guideway, a first spring for urging said syringe holder forward in said guideway, cocking means including an arresting pawl for releaseably holding said syringe holder against the force of said spring in a withdrawn position ready for use, and hand operable means (3) provided in said casing and operable by a single controllable continued interruptable movement of the same hand that holds the casing, to cause the syringe as a whole to be shot forward in response to displacement of said arresting pawl and, thereafter, to operate the syringe by bringing force to bear against the piston-rod (7, 7a) thereof, said hand operable means including:

a push-rod (23) mounted in said casing (2) for longitudinal movement therein and having a front end (23a) arranged for acting on said arresting pawl (17) for displacement thereof, and equipped at its rear end (23b) with hell-mounted means (30) for establishing contact with and bearing directly on the rear end of said piston rod (7, 7a) of said syringe (4) after said arresting pawl has been displaced to release said syringe, said push rod (23) being provided with a rack by engagement of which it may be longitudinally propelled;

a second rod (34) provided with a rack, mounted in said casing for movement parallel to the direction of movement of said push rod;

a rotary gear (38) for communicating movement between said second rod and said push rod, mounted between said rods in said casing and engaging the racks thereof;

a second spring acting on one of said rods so as to oppose forward movement of said push rod;

a pull-trigger (41) rigidly connected to a member of a rod system constituted by said push rod and said second rod, said pull-trigger being part of a slide mounted in said casing so as to be displaceable, with respect to the stationary grip portion (42) of said casing, parallel to the displacement of said rods, the displacement of said trigger being proportional to the the displacement of said piston rod of said syringe when contact is established between said push rod and said piston rod; and a heel (26) on the rear end of said push-rod having an adjusting device (27) thereon for adjustably mounting said means (30) for establishing contact with the piston rod of said syringe, said adjusting device comprising a threaded spindle (28).

2. An intramuscular injection device as defined in claim 1 in which said hand-operated means (3) includes a pivotally mounted intermediate lever (24) in said casing, located therein operatively between said arresting pawl (17) and the path of said push-rod (23) for transfer of force from said push-rod to said pawl.

3. An intramuscular injection device as defined in claim 1 or claim 2, in which a third spring (19) is arranged to bear on said pawl (17) to facilitate cocking said syringe holder in position.

4. An intramuscular injection device as defined in claim 1 or claim 2, in which said guideway is constituted as a removable shell (11) for displaceably containing said syringe holder (9), and in which said casing is provided with means for mounting said shell, and in which, further, said first spring is a tension spring anchorable at one end in a portion of said casing mounting said shell and attachable at its other end to said syringe holder, said shell having an abuttment (48) for the forward position of said syringe holder and also having a head portion (12) provided with an aperture for the passage of the needle of said syringe.

5. An intramuscular injection device as defined in claim 4, in which said shell has a tubular threaded portion and in which said head portion (12) is mounted by screw threads on said threaded portion of said shell, in which, further said shell is equipped with an extension shell (45) seating a container (46) or a sealing cap (50), said extension shell being shaped so that it can be pushed onto or removed from said head portion (12) of said shell.

* * * * *